(12) United States Patent
Howieson et al.

(10) Patent No.: US 8,411,273 B2
(45) Date of Patent: Apr. 2, 2013

(54) MULTI MODE FIBRE PERTURBER

(75) Inventors: Iain Howieson, Stirling (GB); Michael McCulloch, Stirling (GB)

(73) Assignee: Cascade Technologies Limited, Stirling (GB)

( * ) Notice: Subject to any disclaimer, the term of this patent is extended or adjusted under 35 U.S.C. 154(b) by 496 days.

(21) Appl. No.: 12/516,936

(22) PCT Filed: Nov. 12, 2007

(86) PCT No.: PCT/GB2007/004295
§ 371 (c)(1),
(2), (4) Date: May 29, 2009

(87) PCT Pub. No.: WO2008/065336
PCT Pub. Date: Jun. 5, 2008

(65) Prior Publication Data
US 2010/0067013 A1    Mar. 18, 2010

(30) Foreign Application Priority Data
Nov. 29, 2006  (GB) .................................. 0623835.6

(51) Int. Cl.
*G01N 21/00* (2006.01)
(52) U.S. Cl. ..................................................... 356/437
(58) Field of Classification Search .................. None
See application file for complete search history.

(56) References Cited

U.S. PATENT DOCUMENTS

| 6,791,689 B1 * | 9/2004 | Weckstrom ................... 356/437 |
| 7,248,755 B2 * | 7/2007 | Sappey et al. ................... 385/13 |
| 7,787,728 B2 * | 8/2010 | Masterson et al. ........... 356/73.1 |
| 2008/0002186 A1 * | 1/2008 | Masterson et al. ........... 356/73.1 |

FOREIGN PATENT DOCUMENTS

| JP | 2005-522694 | 10/2003 |
| JP | 2006-522938 | 10/2004 |
| WO | WO03087787 A1 | 10/2003 |
| WO | WO2005/103781 A1 | 11/2005 |

OTHER PUBLICATIONS

"The limitations for suppressing modal noise induced in a graded-index multimode fibre in a white light interferometer", Optics Communications, North-Holland Publishing Co., vol. 133, No. 1, Jan. 1, 1997, XP004015716.
International Search Report for PCT/GB2007/004295, dated Feb. 15, 2008.
Office Action issued in Japanese Application No. 2009-538763, dated Nov. 21, 2012.

* cited by examiner

*Primary Examiner* — Gregory J Toatley
*Assistant Examiner* — Juan D Velentin, II
(74) *Attorney, Agent, or Firm* — Moore & Van Allen, PLLC; W. Kevin Ransom

(57) ABSTRACT

An optical arrangement comprising a multi-mode fiber (16) for carrying single mode laser light (12); a randomizer (18) for randomizing spatial modes supported by the fiber and means for averaging, out the randomized spatial modes to recover the single spatial mode.

30 Claims, 1 Drawing Sheet

MULTI MODE FIBRE PERTURBER

FIELD OF THE INVENTION

The present invention relates to a system and method for transmitting single mode light via multi-mode optical fiber, and preferably over long distances. In particular, the invention relates to a fiber coupled gas sensor system for use in remote and/or hostile conditions.

BACKGROUND OF THE INVENTION

Optical fibers have been used as a medium for transmitting light over long distances in applications such as communications. More recently near infra red (IR) optical fibers have been used in gas sensing applications to pipe light to inaccessible or hostile locations. This has allowed multiple point remote gas sensing techniques to be employed. Such laser based gas sensing techniques typically use a single mode laser source to provide high sensitivity and high-resolution measurements. To preserve the spectral properties of the source, the laser output must be transmitted through single mode fiber.

Recently, quantum cascade lasers have been used in gas sensing applications, as described in WO03087787, the contents of which are incorporated herein by reference. The increased cross sections associated with spectroscopic transitions in the mid IR can provide significantly enhanced detection sensitivities. Fiber based mid IR sensors, however, have not typically been used in gas sensing applications due to the excessive losses associated with single mode mid IR fibers. Many of these losses arise because single mode fibers are very narrow, for example, having core diameters around 5-10 $\mu$m, which makes it difficult to efficiently couple light into the fiber. In contrast, multimode fibers typically have core diameters of 400-500 $\mu$m. However, transmission of single mode laser light through a multimode fiber results in multiple spatial modes being supported. Such spatial modes typically interfere at the detector, producing optical interference noise.

SUMMARY OF THE INVENTION

According to one aspect of the present invention, there is provided an optical arrangement comprising a multi-mode fiber for carrying single mode laser light; a randomizer for randomizing spatial modes supported by the fiber, and averaging means for averaging out the randomized spatial modes, thereby to recover the single spatial mode.

Preferably, the randomizer is operable to cause spatial oscillation of the fiber. Rapid spatial oscillation of the multi-mode fiber randomizes the spatial modes that the fiber supports. By signal averaging, the randomized spatial modes can be recombined at the detector and the single spatial mode properties of the laser recovered.

The present invention can be used in many practical applications, but in a preferred embodiment it is used in a gas sensor that comprises a laser, preferably a single mode laser, a multi-mode fiber for transmitting light from the laser to and/or from a target area, a randomizer for randomizing spatial modes supported by the fiber; a detector for detecting light that has passed through the target area and averaging means for averaging out the randomized spatial modes to recover the single spatial mode.

By signal averaging, the randomized spatial modes can be recombined at the detector and the single spatial mode properties of the laser recovered. Therefore, the introduction of optical interference noise is prevented and the high sensitivity of the sensor preserved. This allows a multi mode fiber to be used in sensitive gas sensor applications, thereby avoiding the high losses typically associated with single mode fiber, and providing the ability for multiple point remote detection in inaccessible/hostile locations.

The randomizer may be any suitable arrangement for causing spatial oscillation of the fiber. For example, the randomizer may be a perturber that is operable to cause a physical perturbation along the fiber. For example, the perturber may comprise any one or more of a DC motor with an eccentric weight, a flat panel exciter and a piezoelectric motor. The frequency of the spatial oscillations induced by the perturber may be in the range of 1 Hz to 10 kHz.

Preferably, the laser source is a chirped laser. In this case, the wavelength variation provided by the wavelength chirp itself is used to provide a wavelength scan. Hence, there is no need to tune the effective emission linewidth across a spectral region using, for example, a slow DC current ramp superimposed on the pulse train. This means that sampling rate can be very high and a full spectral analysis can be done very quickly.

The chirped laser may be a semiconductor laser, for example a semiconductor diode laser. The chirped light is generated by applying a one or a series of substantially step function electrical pulses to the semiconductor diode laser to cause the laser to output one or more pulses, each having a continuous wavelength chirp, for injecting into the optical cell. The laser may be a quantum cascade laser.

Each applied pulse has a duration that is greater than 150 ns, in particular greater than 200 ns. Each applied pulse may have a duration that is in the range of 150 to 300 ns, preferably 200 to 300 ns. This can provide a tuning range of about 60 GHz.

Each detected pulse may have a duration that is greater than 150 ns, in particular greater than 200 ns. Preferably, each detected pulse has a duration that is in the range of 150 to 300 ns, preferably 200 to 300 ns.

BRIEF DESCRIPTION OF THE DRAWINGS

Various aspects of the invention will now be described by way of example only and with reference to the accompanying drawings, of which.

SPECIFIC DESCRIPTION OF THE DRAWINGS

Figure 1:
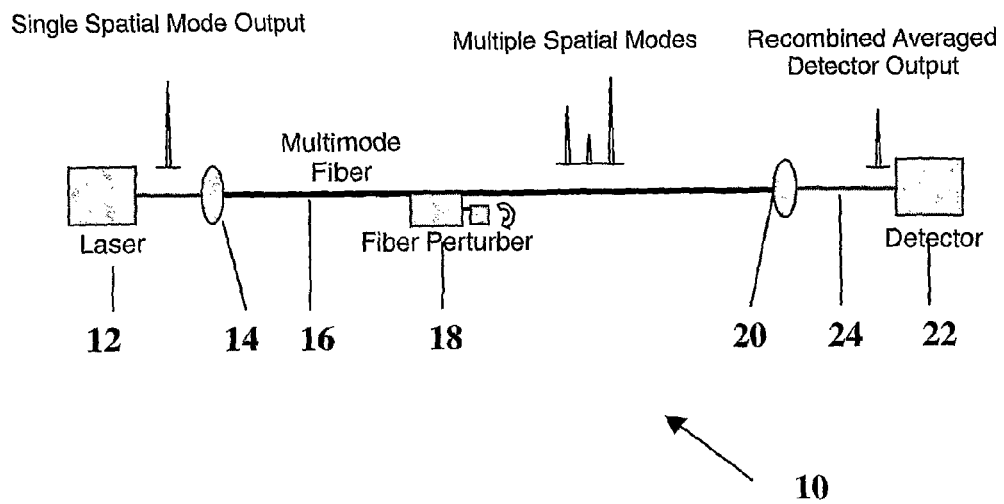
FIG. 1 is a schematic diagram of a first gas sensor.

FIG. 1 shows a multimode fiber quantum cascade gas or particle sensor 10. This has a single mode quantum cascade laser 12 with a convex lens 14 at its output for focussing light into a multimode optical fiber 16. Along its length is a mechanism 18 for spatially perturbing the fiber 16. In this example, the mechanism 18 is a DC motor with an eccentric weight, although other mechanisms to rapidly move the fiber could be used such as flat panel exciters, piezoelectric motors. At the output of the multimode fiber 16 is a convex lens 20 for focussing light towards a detector 22 via a sample area 24. The sample area 24 may be an open cell configuration arranged so that light makes a single pass through it or a cell through which the light passes multiple times before exiting. A description of various quantum cascade gas sensors and specific examples of suitable sample cell configurations are described in WO03087787, the contents of which are incorporated herein by reference.

In use, a step function electrical pulse is applied to the quantum cascade laser 12 to cause it to output a continuous wavelength chirp. Each applied pulse has a duration that is greater than 150 ns, in particular greater than 200 ns and a duration that is in the range of 150 to 300 ns, ideally 200 to 300 ns. The continuous wavelength chirp is injected into the optical fiber, so that it passes through the sample area and into the detector. The wavelength variation provided by each chirp is used as an intra-pulse scan, which can be used to identify gases in the sample area.

Simultaneously with passing the wavelength chirps through the fiber 16, the perturber mechanism 18 is used to cause rapid spatial oscillation of the fiber, these oscillations typically having a frequency in the range of a 1 or 2 Hz to 10 kHz. This has the effect of randomizing the spatial modes that the fiber 16 supports. By signal averaging over a suitable time interval and a suitable number of samples, the randomized spatial modes can be recombined at the detector 22. The time interval for averaging has to be selected to ensure that significant randomization is enabled, and usually will be a few ms to a few seconds. Typically, between 100 and 1000 samples would be sufficient to average out the effect of the randomized spatial modes, so that the single spatial mode properties of the laser can be recovered. The recovered signal can be used to detect or identify gases in the sample area 24, as described, for example, in WO03087787. Typically, this involves comparing the detected signal with one or more fingerprints for know materials.

By randomizing the spatial modes, the introduction of optical interference noise due to the multi-mode fiber 16 is prevented and the high sensitivity of the sensor can be preserved, whilst avoiding the need for a single mode fiber. As well as this, the ability to rapidly change the interference pattern of a propagating beam travelling through free space via multimode fiber perturbation allows for the removal of optical interference noise generated from external sources such as windows or from scintillation/turbulence. This has significant impact both in open path gas sensing as well as free space telecoms, where interference noise severely impacts the ultimate performance of the system.

The present invention provides numerous practical advantages. In particular, it allows the use of multimode optical fibers in applications that require single mode performance. Multimode fiber provides broadband coverage enabling multiple laser wavelengths to be transmitted by one carrier. This significantly reduces fiber and installation costs for laser based sensing applications. Coupling and transmission losses are lower with multimode fiber, which enables relatively long distance fiber runs, thereby providing the opportunity for multiple point remote detection. Furthermore, the large core diameters of multi-mode fibers can be exploited to significantly reduce the opto-mechanical alignment tolerances between the laser and fiber itself. This reduces the packaging costs of the laser and fiber and provides the opportunity for significant increases in instrument robustness. Since gas sensors are often located in hostile or difficult environments, this is a significant advantage.

Figure 2:
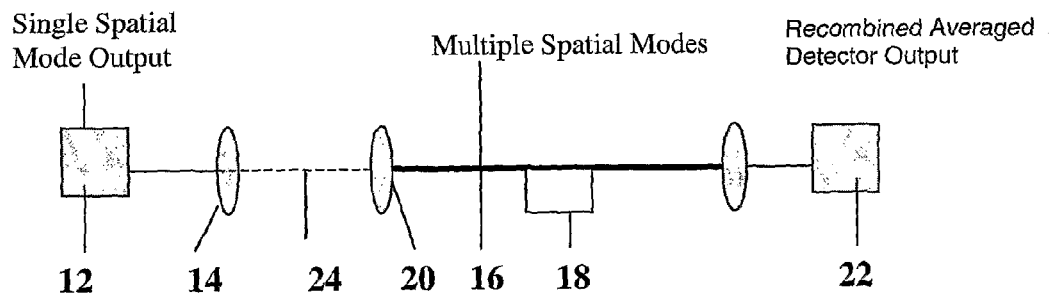
FIG. 2 is a schematic diagram of a second gas sensor.

A skilled person will appreciate that variations of the disclosed arrangements are possible without departing from the invention. For example, whilst the perturber of FIG. 1 is shown positioned along the length of the fiber at the output of the laser so that the fiber is perturbed downstream of the sample area, it could equally be provided along a length of fiber positioned between the sample area and the detector, as shown in FIG. 2, so that is it perturbed upstream. Equally, a combination of the arrangements of FIGS. 1 and 2 could be used, in which the fiber is perturbed both downstream and upstream of the sample area. Accordingly the above description of the specific embodiment is made by way of example only and not for the purposes of limitation. It is clear that minor modifications may be made without significant changes to the operation described.

The invention claimed is:

1. An optical arrangement for sensing a gas, said optical arrangement comprising:
    a quantum cascade chirped laser that outputs a wavelength chirp for providing a wavelength scan;
    a multi-mode fiber positioned between said laser and a target area and having a first end optically coupled to said laser, wherein said multi-mode fiber is configured for transmitting light from the laser to and/or from the target area for sensing a gas located at the target area;
    a randomizer adjacent said multi-mode fiber for randomizing spatial modes supported by the multi-mode fiber;
    a detector spaced apart from said target area for detecting light emitted from a second end of said multi-mode fiber and that has passed through the target area, wherein said detector is configured to average out randomized spatial modes to recover a single spatial mode.

2. An arrangement as claimed in claim 1 wherein the randomizer is operable to cause spatial oscillation of the multi-mode fiber.

3. An arrangement as claimed in claim 2 wherein the randomizer is operable to cause a physical perturbation along the multi-mode fiber.

4. An arrangement as claimed in claim 3 wherein the randomizer comprises any one or more of a DC motor with an eccentric weight, a flat panel exciter, or a piezoelectric motor.

5. An arrangement as claimed in claim 2 wherein the frequency of the spatial oscillation is in the range of approximately 1 Hz to 10 kHz.

6. An arrangement as claimed in claim 1 wherein the detector is configured to average out randomized spatial modes to recover a single spatial mode using between one hundred and one thousand samples.

7. An arrangement as claimed in claim 1 wherein the chirped laser comprises a semiconductor laser.

8. An arrangement as claimed in claim 1 wherein the chirped laser comprises a semiconductor diode laser.

9. An arrangement as claimed in claim 1 comprising means for applying one or more substantially step function electrical pulses to the chirped laser to cause the chirped laser to output one or more light pulses for injecting into an optical cell, wherein each of the one or more light pulses comprises a continuous wavelength chirp.

10. An arrangement as claimed in claim 9 wherein each of the one or more light pulses has a duration greater than approximately 150 ns.

11. An arrangement as claimed in claim 10 wherein each of the one or more light pulses has a duration in the range of approximately 150 to 300 ns.

12. An arrangement as claimed in claim 9 wherein a detected pulse duration is greater than approximately 150 ns.

13. An arrangement as claimed in claim 9 wherein a detected pulse duration is in the range of approximately 150 to 300 ns.

14. A gas sensor comprising:
    a quantum cascade chirped laser that outputs a wavelength chirp for providing a wavelength scan;
    a multi-mode fiber positioned between said laser and a target area and having a first end optically coupled to said laser, wherein said multi-mode fiber is configured for transmitting light from the laser to and/or from the target area for sensing a gas located at the target area;

a randomizer adjacent said multi-mode fiber for randomizing spatial modes supported by the multi-mode fiber;

a detector spaced apart from said target area for detecting light emitted from a second end of said multi-mode fiber and that has passed through the target area, wherein said detector is configured to average out randomized spatial modes to recover a single spatial mode.

15. A gas sensor as claimed in claim 14 wherein the randomizer is operable to cause spatial oscillation of the multi-mode fiber.

16. A gas sensor as claimed in claim 15 wherein the randomizer is operable to cause a physical perturbation along the multi-mode fiber.

17. A gas sensor as claimed in claim 16 wherein the randomizer comprises any one or more of a DC motor with an eccentric weight, a flat panel exciter, or a piezoelectric motor.

18. A gas sensor as claimed in claim 15 wherein the frequency of the spatial oscillation is in the range of approximately 1 to 10 kHz.

19. A gas sensor as claimed in claim 14 wherein the detector is configured to average out randomized spatial modes to recover a single spatial mode using between one hundred and one thousand samples.

20. A gas sensor as claimed in claim 14 wherein the chirped laser comprises a semiconductor laser.

21. A gas sensor as claimed in claim 14 wherein the chirped laser comprises a semiconductor diode laser.

22. A gas sensor as claimed in claim 14 comprising means for applying one or more substantially step function electrical pulses to the chirped laser to cause the chirped laser to output one or more light pulses for injecting into an optical cell, wherein each of the one or more light pulses comprises a continuous wavelength chirp.

23. A gas sensor as claimed in claim 22 wherein each of the one or more light pulses has a duration greater than approximately 150 ns.

24. A gas sensor as claimed in claim 22 wherein each of the one or more light pulses has a duration in the range of approximately 150 to 300 ns.

25. A gas sensor as claimed in claim 22 wherein a detected pulse duration is greater than approximately 150 ns.

26. A gas sensor as claimed in claim 22 wherein a detected pulse duration is in the range of approximately 150 to 300 ns.

27. A gas sensor as claimed in claim 14 wherein the randomizer is provided upstream of the target area.

28. A gas sensor as claimed in claim 14 wherein the randomizer is provided downstream of the target area.

29. A method for sensing a gas, said method comprising:

transmitting light from a single mode laser, wherein the laser is a quantum cascade chirped laser that outputs a wavelength chirp for providing a wavelength scan;

directing the light from the laser at a multi-mode fiber positioned between the laser and a target area and having a first end optically coupled to the laser, wherein the multi-mode fiber is configured for transmitting light from the laser to and/or from the target area for sensing a gas located at the target area;

randomizing spatial modes supported by the multi-mode fiber using a randomizer adjacent said multi-mode fiber; and averaging out randomized spatial modes to recover a single spatial mode using a detector spaced apart from said target area for detecting light emitted from a second end of said multi-mode fiber and that has passed through the target area.

30. A method as claimed in claim 29 wherein the radiation is transmitted at least in part through free space.

* * * * *